(12) United States Patent
Southworth

(10) Patent No.: US 7,763,080 B2
(45) Date of Patent: Jul. 27, 2010

(54) IMPLANT SYSTEM WITH MIGRATION MEASUREMENT CAPACITY

(75) Inventor: Carleton B. Southworth, Warsaw, IN (US)

(73) Assignee: Depuy Products, Inc., Warsaw, IN (US)

( * ) Notice: Subject to any disclaimer, the term of this patent is extended or adjusted under 35 U.S.C. 154(b) by 273 days.

(21) Appl. No.: 10/836,473

(22) Filed: Apr. 30, 2004

(65) Prior Publication Data

US 2005/0246020 A1 Nov. 3, 2005

(51) Int. Cl.
*A61B 17/58* (2006.01)
(52) U.S. Cl. .................. 623/23.15; 623/23.18; 623/22.4
(58) Field of Classification Search .............. 623/23.15, 623/23.18, 20.14–16, 20.19, 21, 20.25, 20.32–36, 623/22.11, 22.4–43, 22.46, 23.26, 23.44–45
See application file for complete search history.

(56) References Cited

U.S. PATENT DOCUMENTS

| | | | | |
|---|---|---|---|---|
| 2,742,705 A | * | 4/1956 | Gelardi | 33/758 |
| 2,845,715 A | * | 8/1958 | Twardowski | 33/27.032 |
| 5,057,103 A | * | 10/1991 | Davis | 606/63 |
| 5,078,746 A | * | 1/1992 | Garner | 623/23.48 |
| 5,133,760 A | * | 7/1992 | Petersen et al. | 623/20.36 |
| 5,192,283 A | * | 3/1993 | Ling et al. | 606/93 |
| 5,201,882 A | * | 4/1993 | Paxson | 623/22.42 |
| 5,425,768 A | * | 6/1995 | Carpenter et al. | 623/23.48 |
| 5,507,817 A | * | 4/1996 | Craig et al. | 623/20.11 |
| 5,888,210 A | * | 3/1999 | Draenert | 623/23.35 |
| 6,428,578 B2 | * | 8/2002 | White | 623/23.22 |
| 2001/0020187 A1 | * | 9/2001 | Guettinger et al. | 623/23.25 |
| 2004/0107002 A1 | * | 6/2004 | Katsuya | 623/23.25 |

\* cited by examiner

*Primary Examiner*—Eduardo C Robert
*Assistant Examiner*—Mary Hoffman

(57) ABSTRACT

Position reference members are provided as part of an orthopaedic implant system. Both position reference members can be implanted on or in the same bone as the other parts of the implant. One of the position reference members is fixed to the bone and the other position reference member is movable with another part of the implant, such as a stem received in the intramedullary canal. The movable position reference member can move with respect to the fixed position reference member. At least one of the position reference members includes indicia such as a main scale or a vernier scale. Parts of the indicia and position reference members are radioopaque and parts are radiolucent. Post-operative changes in the relative positions of the position reference members can be measured by radiography or fluoroscopy so that changes in the implant position can be monitored over time.

3 Claims, 6 Drawing Sheets

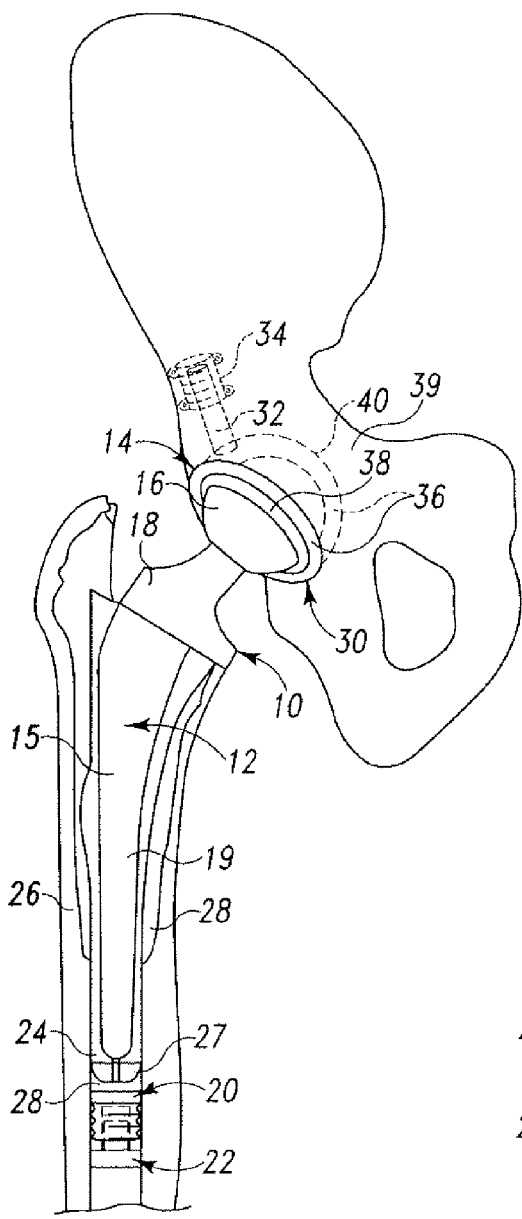
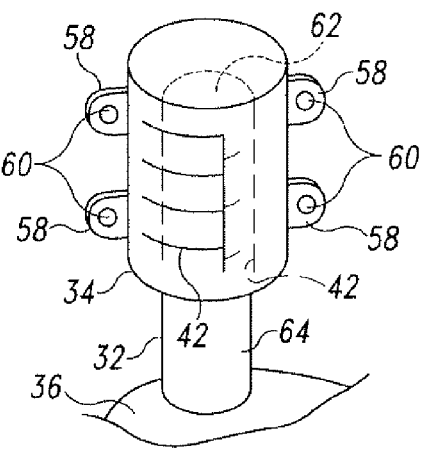
Fig. 2
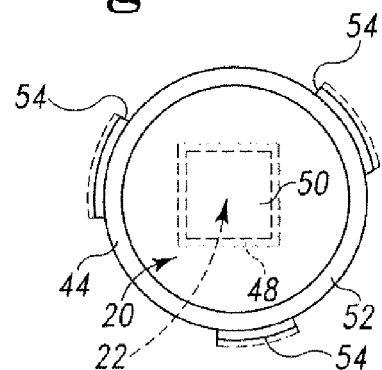
Fig. 3
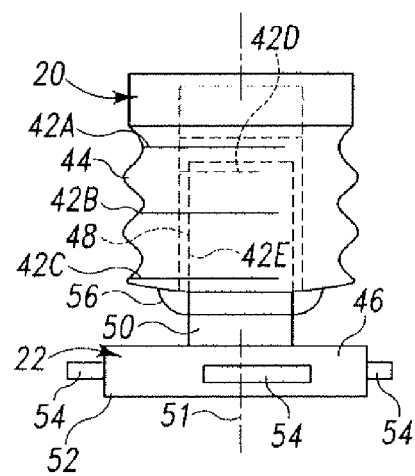
Fig. 1    Fig. 4

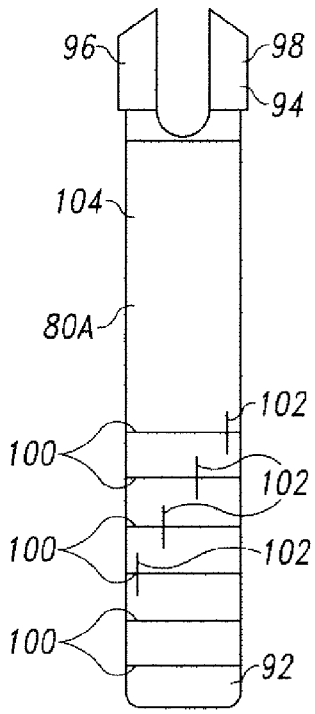 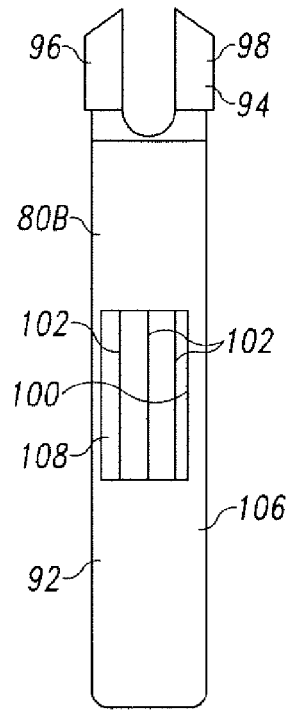 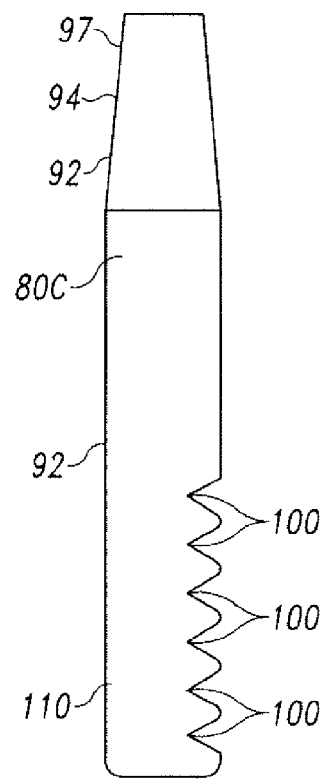
Fig. 10  Fig. 11  Fig. 12
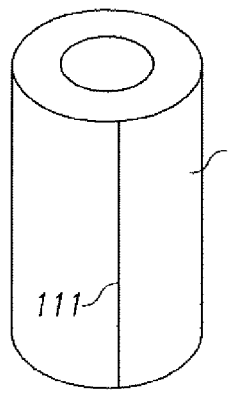 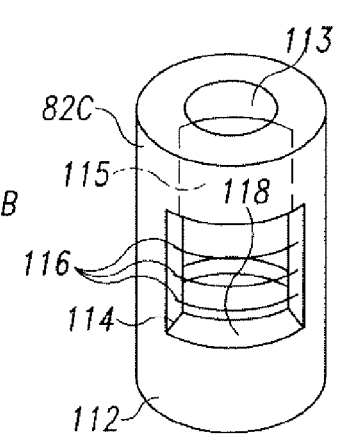 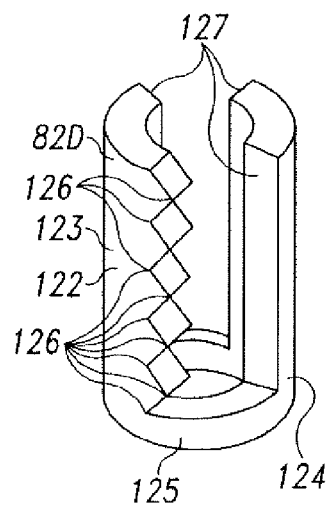
Fig. 13  Fig. 14  Fig. 15

IMPLANT SYSTEM WITH MIGRATION MEASUREMENT CAPACITY

TECHNICAL FIELD OF THE INVENTION

The present invention relates to implant systems for use in treating the skeletal systems of human patients, and more particularly, to prosthetic joints used in replacing parts of human joints, such as the hip, knee, shoulder, ankle and elbow.

BACKGROUND OF THE INVENTION

Human joints can become damaged as a result of accident or illness. Such damage can be, for example, to the articular cartilage covering the ends of the bones at the joint as well as the intra-articular cartilage between the ends of the adjacent bones of the joint. When the damage to the joint is severe, a prosthetic joint can be implanted to improve the comfort and mobility of the patient.

Prosthetic joints have been developed to replace native tissue of several human joints. There are a variety of knee prostheses, hip prostheses, shoulder prostheses, ankle prostheses, elbow prostheses and wrist prostheses available to relieve patient suffering. Such devices are available, for example, from the assignee of the present invention, DePuy Orthopaedics, Inc. of Warsaw, Ind.

Standard prosthetic joints include metal components that are affixed to the articulating ends of the bones of the joint and commonly include a bearing component positioned between the metal components. Standard bearing components of prosthetic joints have a surface against which one of the metal components articulates. For example, hip endoprostheses include a metal femoral component to be affixed to the proximal femur and a metal cup to be affixed to the acetabulum. Many of these standard hip endoprostheses include a liner in the acetabular cup against which the femoral component articulates. Knee prostheses commonly include a femoral component to be affixed to the distal femur and a tibial component to be affixed to the proximal tibia. Bearings are typically between the femoral and tibial components.

An important consideration in the design, manufacture and implantation of any of these joint prostheses is adequate fixation of the bone-contacting prosthetic components to the native bone. Some designs of joint prostheses call for cemented fixation of prosthetic components to the native bone, using bone cement such as polymethylmethacrylate. Some designs encourage the ingrowth of hard tissue (that is, bone) around and onto the prosthetic component through the provision of porous outer surfaces on parts of the prosthetic component.

Even with the use of bone cement and porous surfaces, it is possible for a prosthetic joint implant to become loose over time. Loose bone-contacting components of a joint prosthesis (for example, stems received in the intramedullary canal) can become painful for the patient, and such loosening can eventually require revision surgery.

Movement of the bone-contacting components is a prognostic indicator of potential fixation failure through loosening (either implant to bone fixation, implant to cement fixation, or cement to bone fixation). However, accurate measurement of movement of bone-contacting prosthetic joint components can be problematic. Standard radiographs taken at different times (for example, immediately post-surgery and several months post-surgery) can be compared, but it would be difficult to detect small movements of the joint components accurately. More sophisticated techniques can also be used, but can be costly and can require special equipment. For example, radiostereometry analysis could be used, but this method requires that tantalum beads be implanted and requires software and expertise to obtain an accurate measurement of implant movement. It is believed that computer software is also being developed to measure implant migration through CT scans, but this method will also require additional equipment and expertise. In addition, the more sophisticated measurement techniques may expose the patient to additional radiation. Methods of evaluating implant loosening in the context of prosthetic hip joints are described in JOINT REPLACEMENT ARTHROPLASTY, $3^{rd}$ ed. 2003, in Chapter 61, pp. 811-823, edited by Bernard F. Morrey, M.D., incorporated by reference herein.

SUMMARY OF THE INVENTION

The need for a way to determine whether an implant component has migrated, and to measure the extent of migration when it has occurred is addressed by the present invention. In the present invention, this need can be addressed using standard radiography and fluoroscopy.

In one aspect, the present invention provides an implant system for fixation to a bone. The implant system comprises an implant component for fixation to the bone, a first position reference member and a second position reference member. The first position reference member is sized and shaped to be capable of being implanted proximate to the implant component. The second position reference member is sized and shaped to be capable of being implanted proximate to the first position reference. The first position reference member and the second position reference member are sized and shaped to be capable of relative movement. At least one of the first position reference member and second position reference member includes indicia. The first position reference member, second position reference member and indicia are sized, shaped and made of a material such that post-operative changes in the relative positions of the first position reference member and second position reference member can be determined by radiography or fluoroscopy.

In another aspect, the present invention provides a prosthetic system implanted on a bone. The prosthetic system comprises a prosthetic component implanted on the bone, a movable position reference member and a fixed position reference member. The movable position reference member is implanted proximate to the prosthetic component and is movable with respect to the bone with movement of the prosthetic component with respect to the bone. The fixed position reference member is implanted proximate to the movable position reference. At least one of the position reference members includes indicia. The position reference members and indicia are sized, shaped and made of a material such that post-operative changes in the relative positions of the position reference members can be determined by radiography or fluoroscopy.

BRIEF DESCRIPTION OF THE DRAWINGS

FIG. 1 is a diagrammatic illustration of a prosthetic hip joint implanted on the hip bone and proximal femur, with the femoral stem cemented in place in the intramedullary canal, with the proximal femur and bone cement shown in cross-section along a coronal plane, and illustrating two embodiments of fixed position reference members and complementary movable position reference members;

FIG. 2 is a perspective view of one of the fixed position reference members of FIG. 1 and its complementary movable position reference member, shown in use with an acetabular implant component;

FIG. 3 is a plan view of an assembly of the other fixed position reference member of FIG. 1, shown prior to implantation with its complementary movable position reference member;

FIG. 4 is an elevation of the assembly of FIG. 3;

FIG. 10 is an elevation of one possible movable position reference member suitable for use in conjunction with an orthopaedic implant such as the proximal femoral stem shown in FIG. 7;

FIG. 11 is an elevation of another possible movable position reference member suitable for use in conjunction with an orthopaedic implant such as the proximal femoral stem shown in FIG. 7;

FIG. 12 is an elevation of another possible movable position reference member suitable for use in conjunction with an orthopaedic implant such as the proximal femoral stem shown in FIG. 7;

FIG. 13 is a perspective view of another possible fixed position reference member suitable for use in conjunction with an orthopaedic implant such as the proximal femoral stem shown in FIG. 7;

FIG. 14 is a perspective view of another possible fixed position reference member suitable for use in conjunction with an orthopaedic implant such as the proximal femoral stem shown in FIG. 7;

FIG. 15 is a perspective view of another possible fixed position reference member suitable for use in conjunction with an orthopaedic implant such as the proximal femoral stem shown in FIG. 7;

DETAILED DESCRIPTION OF THE INVENTION

Figures 5, 6:
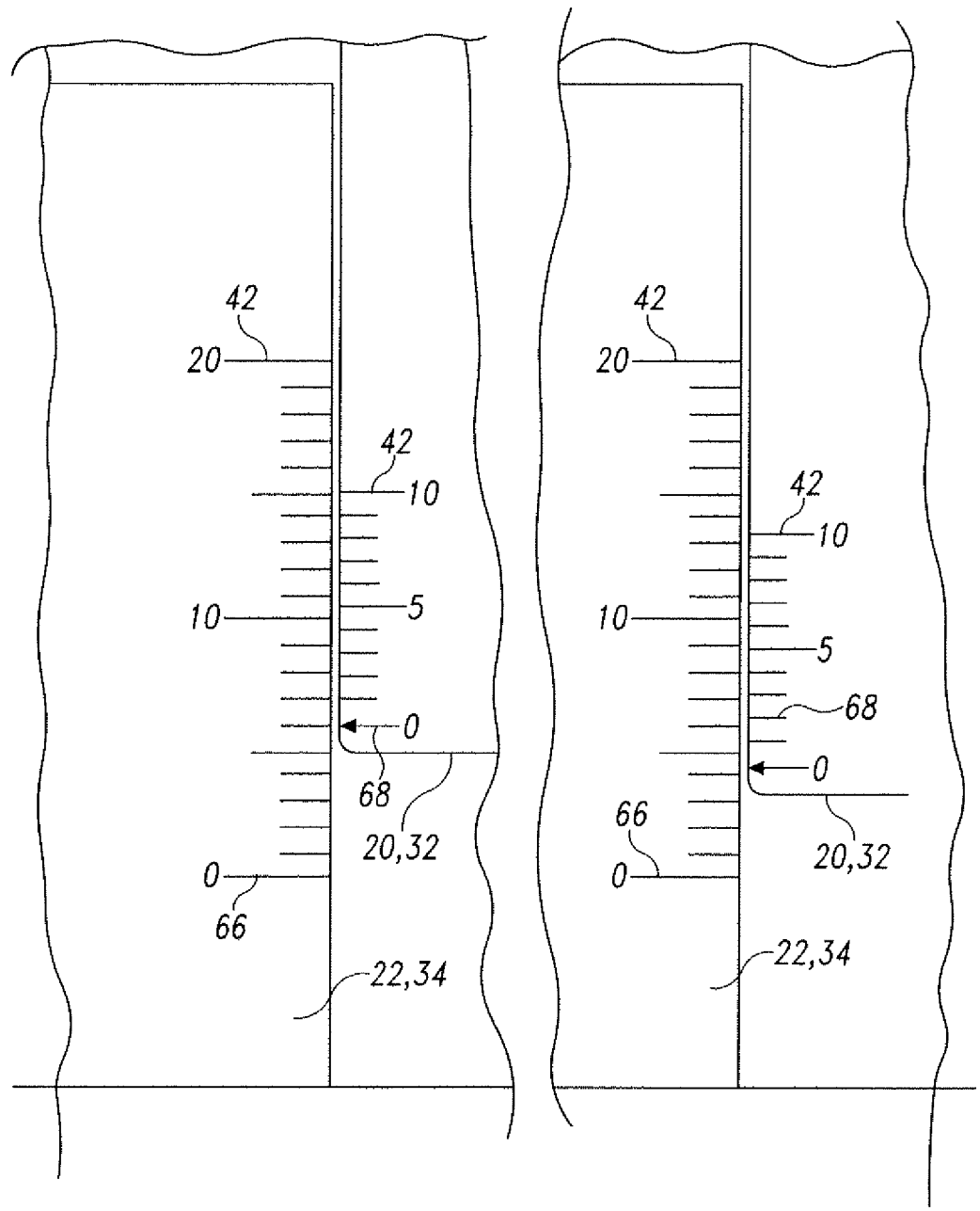
FIG. 5 is an enlarged view of a possible embodiment of indicia provided on a fixed position reference member and indicia on a movable position reference member, shown at one point in time, illustrating use of complementary vernier and main scales as indicia.
FIG. 6 is an enlarged view of the indicia of FIG. 5 shown at a different point in time, illustrating how a vernier indicia system could be used to determine the extent of undesirable movement of an implant with respect to the bone over time.

Embodiments of the present invention and the advantages thereof are best understood by referring to the following description and drawings, wherein like numerals are used for like and corresponding parts of the drawings.

A first embodiment of an orthopaedic implant system illustrating the principles of the present invention is illustrated in FIGS. 1-4. The first illustrated joint implant system 10 comprises a prosthetic hip joint. The illustrated prosthetic hip joint includes a proximal femoral system 12 and an acetabular system 14.

The first illustrated proximal femoral system 12 includes a proximal femoral implant component 15. The proximal femoral implant component 15 includes a femoral head 16 and a femoral stem 18. The femoral head 16 comprises an articulating portion of the proximal femoral implant component 15 and the femoral stem 18 comprises a fixation portion 19. The femoral head 16 is substantially spherical and is assembled with the femoral stem 18 in a standard manner. The proximal femoral implant system 12 also includes a movable femoral position reference member 20 and a fixed femoral position reference member 22.

The fixation portion 19 of the femoral stem 18 is at the distal end of the stem, and is generally sized and shaped to be received within the intramedullary canal 24 of the proximal femur 26. In the embodiment of FIG. 1, a centralizer 27 is provided at the distal end of the femoral stem 18. In the first illustrated embodiment, the femoral stem 18 is sized, shaped and has a surface finish suitable for cemented fixation in the intramedullary canal 24. Bone cement is shown at 28 in FIG. 1.

The femoral head 16 is received within and articulates against part of the acetabular system 14. The acetabular system 14 comprises an acetabular implant component 30, a movable acetabular position reference member 32 and a fixed acetabular position reference member 34. The illustrated acetabular implant component 30 is an assembly of an acetabular shell 36 and a liner 38. The acetabular shell 36 includes a fixation portion 40 defined by the outer surface of the shell; the shell 36 is received within and fixed to the acetabulum of the hip bone (or innominate bone) 39. The liner 38 comprises the articulating portion of the acetabular component 30, against which the femoral head 16 bears.

The proximal femoral stem 18, femoral head 16, acetabular shell 36 and acetabular liner 38 may have features of standard commercially available prosthetic hip joints, such as those available from DePuy Orthopaedics, Inc. of Warsaw, Ind. It should be understood that these systems are identified for purposes of illustration only; the present invention is expected to have application to the systems available from other suppliers of orthopaedic implants. In addition, the present invention is expected to have application to future implant systems as well as those presently available. Accordingly, the present invention is not limited to the system or configuration of any particular orthopaedic implant system unless expressly called for in the claims. As described in more detail below, the present invention is applicable to all such systems whether designed for cemented fixation or for fixation through bony ingrowth. In addition, the proximal femoral stem 18, femoral head 16 and parts 36, 38 of the acetabular implant component 30 may be made of standard materials; for example, the proximal femoral stem 18 and acetabular shell 36 may be made of titanium or a cobalt-chrome alloy; the femoral head 16 could be made of a standard metal, such as titanium or cobalt-chrome alloy, or could be made of ceramic; the acetabular liner 38 could be made of ultrahigh molecular weight polyethylene (including highly cross-linked UHMWPE), standard metal or ceramic, for example.

It should be understood that the present invention is not limited to hip implant systems. As described in more detail below, the principles of the present invention are also expected to apply to prosthetic knee systems, prosthetic shoulder systems, prosthetic ankle systems, prosthetic wrist systems, prosthetic elbow systems and potentially to spinal implants as well. Moreover, as additional orthopaedic implant systems are developed, the principles of the present invention may also be useful; for example, if a transmandibular prosthetic joint is developed to replace a portion of the jaw, the present invention has potential applicability.

Referring back to the proximal femoral implant system 12 and acetabular implant system 14 illustrated in FIG. 1, both the femoral position reference members 20, 22 of the proximal femoral implant system 12 and the acetabular position reference members 32, 34 of the acetabular implant system are sized and shaped to be implantable within their respective bones 26, 39. In addition, the two femoral position reference members 20, 22 are sized and shaped to be capable of relative movement, and the two acetabular position reference members 32, 34 are sized and shaped to be capable of relative movement, as described in more detail below.

In the first illustrated embodiment, all of the position reference members 20, 22, 32, 34 include indicia 42. All of the position reference members 20, 22, 32, 34 and indicia 42 are sized, shaped and made of a material such that post-operative changes in the relative positions of the associated reference members 20, 22 and 32, 34 can be determined by radiography.

As described in more detail below, a variety of elements could be used for the indicia. For example, the indicia may comprise one or more reference lines, numbers or letters associated with a scale, or teeth or indentations. In addition, the indicia may be oriented or configured to allow for tracking longitudinal movement of an implant component with respect to the bone, rotational movement of an implant component with respect to the bone, or pivoting movement of the implant component with respect to the bone. Accordingly, the present invention should not be considered to be limited to any of the particular illustrated indicia or orientation of indicia unless expressly specified in the claims.

Also as described in more detail below, a variety of structures and materials may be used for the position reference members 20, 22, 32, 34. For example, the fixed position reference members 22, 34 could comprise: a base and post assembly (see FIGS. 1 and 4); a tube (see FIGS. 1, 2, 8-9 and 13); or various portions of a tube (see FIGS. 15-17). The movable position reference members 20, 32 could comprise, for example: a modified cement restrictor (see FIGS. 1 and 3-4); a post to be connected to the implant component (see FIGS. 2, 10-12 and 16-17) or a post integral with the implant component. Moreover, the position reference members 20, 22, 32, 34 could be made of radiolucent materials or could be made of radio-opaque materials with aligned cut-outs to create radiolucent portions. Accordingly, the present invention should not be considered to be limited to any of the particular illustrated structures or materials for the position reference members 20, 22, 32, 34 unless expressly specified in the claims.

Referring now to the particular structures illustrated for the position reference members 20, 22, 32, 34, a first example is illustrated in FIGS. 1 and 3-4. In this example, the femoral position reference members 20, 22 comprise a modified cement restrictor 44 as the movable position reference member 20 and a post 50 and base 52 combination as the fixed position reference member 22.

The modified cement restrictor 44 illustrated in FIGS. 1 and 3-4 is made of a radiolucent material, and includes a plurality of spaced, parallel radio-opaque transverse indicia 42A, 42B, 42C. The modified cement restrictor 44 also has an inner wall defining a blind channel 48 that telescopically receives a post 50 of the fixed position reference member 22. The post 50 and blind channel 48 are square-shaped in transverse cross-section in this embodiment to prevent relative rotation along their central longitudinal axes 51.

The post 50 of the first fixed reference member 22 is fixed to a base 52 that has an enlarged transverse dimension. The base 52 includes a plurality of movable members 54 for fixing the position of the base 52 in the intramedullary canal 24

The post 50 of the first illustrated fixed position reference member is at least partially radiolucent and includes radio-opaque indicia 42D, 42E. Although not visible in FIG. 4, an additional indicia may be aligned with the indicia 42B. In this embodiment, the radio-opaque indicia 42D, 42E are provided in a radiolucent portion of the post, and comprise spaced, parallel lines.

The radio-opaque indicia may be formed of any suitable biocompatible material. The radio-opaque indicia may comprise, for example, thin metal wires, such as stainless steel, titanium, cobalt-chrome alloy, silver or tantulum wires. Alternatively, radio-opaque powders, inks or coatings could be used. A radio-opaque powder, ink, film or coating could be adhered to or imprinted onto the position reference members in known ways. It is anticipated that one of ordinary skill in the art could contact one in the business of medical imprinting to devise a suitable material and method for permanently marking the position reference members. Those in the medical imprinting business include, for example, CI Medical Imprinting Technology of Norton, Mass. and Lightek Corp. of Waukegan, Ill.

It should be understood that the present invention is not limited to any particular degree of radio-opacity for the indicia unless expressly set forth in the claims. Generally, the term "radio-opaque" is used herein to denote a material that can be readily viewed fluoroscopically or radiographically by the surgeon. In general, the radio-opaque portions should be visually distinguishable from the radiolucent portions of the position reference members when the surgeon views the fluoroscopic or radiographic image.

All or part of the post 50 can be made of a radiolucent material. The radiolucent material can be any standard medical grade radiolucent plastic material. For example, the post 50 could be made of ultrahigh molecular weight polyethylene, bone plug material, polymethylmethacrylate or silicone for example. Alternatively, as described in more detail below with respect to the embodiment of FIG. 11, the post 50 could be any standard medical grade metal with holes or fenestrations to provide radiolucent areas corresponding with the radio-opaque indicia.

In the first illustrated embodiment, as shown in FIG. 4, the indicia 42A, 42B, 42C, 42D and 42E extend across only a portion of the outer surfaces of the modified cement restrictor 44 and post 50. If the indicia were to extend around the entire surfaces of the position reference members, both the front and back of each indicia could be visible during fluoroscopy or radiography, and the image could be difficult to read and evaluate. However, it should be understood that the invention is not limited to any particular size or shape of indicia unless expressly set forth in the claims.

For the position reference members 20, 22 of FIG. 1 to be useful post-operatively to track movement of the implant component (e.g. femoral stem 18), the movable position reference member 20 should move if and when the associated implant component (e.g. femoral stem 18) moves with respect to the bone and the fixed position reference member 22 should remain in a fixed position with respect to the bone if and when the associated implant component moves with respect to the bone. It should be understood that any post-operative movement (e.g. migration, subsidence, twisting or canting) of the implant component with respect to the bone is not desired in most implant systems (although there may be implant systems where some subsidence might be desirable); however, to the extent that such undesirable movement of the implant component occurs, the movable position reference member also moves, and the combination of the fixed and movable reference members allows the surgeon to track and measure this undesirable movement.

To fix the position of the fixed position reference member with respect to the bone, movable members such as those shown at 54 in FIG. 4 on the base 52 can be used. The illustrated movable members 54 comprise ribs having a first shape when implanted and a second shape of enlarged diameter after implantation. A shape-memory material, such as Nitinol nickel-titanium alloy could be used for the movable members 54. Thus, for example, when the movable members 54 of the position reference member 22 reach body temperature, their outer diameters could expand from that shown in solid lines in FIGS. 3-4 to that shown in phantom in FIGS. 3-4. With the increased diameter, the movable members 54 could then lock onto the walls of the intramedullary canal 24 to fix the position of the reference member 22 in the intramedullary canal.

For ease of implantation, the position reference members 20, 22 could be provided as an assembly prior to implantation, with the position reference members 20, 22 becoming disassembled after implantation. In the first illustrated embodiment, a shape-memory clip 56 (see FIG. 4) is provided on one of the position reference members, such as on post 50 of fixed position reference member 22. The clip 56 could engage the movable position reference member 20 to hold the two position reference members 20, 22 together temporarily until after implantation. When the clip 56 reaches body temperature, the shape of the clip 56 could change so that the position reference members 20, 22 become disengaged from one another so that relative movement between the position reference members 20, 22 becomes possible. Thus, the clip 56 temporarily holds the two position members 20, 22 together as an assembly until some time after implantation. Alternatively, a material such as gelatin could be used to temporarily hold the two position reference members 20, 22 together; the gelatin may dissolve when it reaches body temperature so that the two position members 20, 22 become disengaged to allow for relative movement.

An alternative example of position reference members is illustrated in FIG. 1 as part of the acetabular system 14. As shown in FIG. 2, the illustrated acetabular position reference members 32, 34 have a different structure than the first illustrated femoral position reference members 20, 22. The fixed acetabular position reference member 34 has flanges 58 with holes 60 for receiving bone screws (not shown) for fixing the fixed acetabular position reference member 32 to the hip bone 39. As in the first illustrated femoral position reference members 20, 22, the fixed acetabular position reference member 34 has a blind bore 62 that telescopically receives a post 64 of the other acetabular position reference member 32. However, in the embodiment of FIG. 2, the post 64 is part of the movable position reference member rather than the fixed position reference member.

Also as in the first illustrated femoral position reference members 20, 22, the indicia 42 of the illustrated acetabular reference members are provided on both acetabular reference members 32, 34. As shown in FIG. 2, the illustrated acetabular indicia 42 comprise a plurality of spaced lines, and may be made of a radio-opaque material. Both of the acetabular position reference members 32, 34 can be made of a radiolucent material, or could be made of a non-radiolucent material but having radiolucent areas that allow post-operative observation of the indicia 42 through fluoroscopy or radiography.

For any of the illustrated position reference members 20, 22, 32, 34, the indicia 42 may comprise a vernier system for determining changes in the relative positions of the fixed reference members 22, 34 and movable reference members 20, 32. An example of a vernier system is illustrated in FIGS. 5-6. As there shown, the indicia on one of the reference members, such as the fixed reference members 22, 34, may comprise a main scale 66, and the indicia on the other reference member, such as the movable reference members 20, 32, may comprise a vernier scale 68. Thus, the indicia of the two position reference members may comprise both lines and numbers that are visible through fluoroscopy or radiography.

FIG. 5 represents a radiographic or fluoroscopic view of the indicia 42 of one of the complementary sets of position references, such as set 20, 22 or set 32, 34, at an initial position and FIG. 6 represents a radiographic or fluoroscopic view of the indicia of that same set of position reference members at a later time or date. At the initial position shown in FIG. 5, the "0" mark on the vernier scale 68 aligns with the position "6" on the main scale 66. At the later position shown in FIG. 6, the "0" mark on the vernier scale 68 is between the "4" and "5" positions on the main scale; since the vernier "5" mark most closely aligns with one of the lines on the main scale, the position of position reference 20, 32 now corresponds with the position "4.5" on the main scale. Thus, in comparing the two images, the surgeon or other caregiver can determine that the position of the movable position reference 20 or 32 has changed by 1.5 units over time. These units could be, for example, millimeters. Thus, the surgeon could thereby determine that the movable position reference member 20 or 32 has moved 1.5 mm over time.

In both of the first illustrated sets of position reference members 20, 22, 32, 34, the position of the movable position reference member 20, 32 corresponds with the position of the associated prosthetic implant, such as femoral stem 18 or acetabular shell 36. In the case of the first illustrated femoral stem 18 and movable femoral position reference member 20, there is bone cement present between the distal end of the femoral stem 18 and the proximal end of the movable position reference member 20 (cement restrictor 44). Subsidence or migration of the femoral stem 18 should cause the bone cement to act against the movable position reference member 20, causing the movable position member 20 to also subside or migrate. Thus, subsidence or migration of the femoral stem 18 indirectly causes subsidence or migration of the movable position member 20. In the case of the first illustrated acetabular shell 36, the movable post 64 of the movable position reference member 32 is directly connected to the shell 36 so that movement of the shell 36 directly causes like movement of the post 64. It should be understood that although the movable femoral position indicator 20 (cement restrictor 44) is illustrated as being separate from the femoral stem 18, there could be a direct connection between these components; for example, the movable femoral position indicator 20 could be directly coupled to the centralizer 27 so that movement of the femoral stem 18 is directly translated to movement of the movable femoral position indicator 20.

Figure 7:
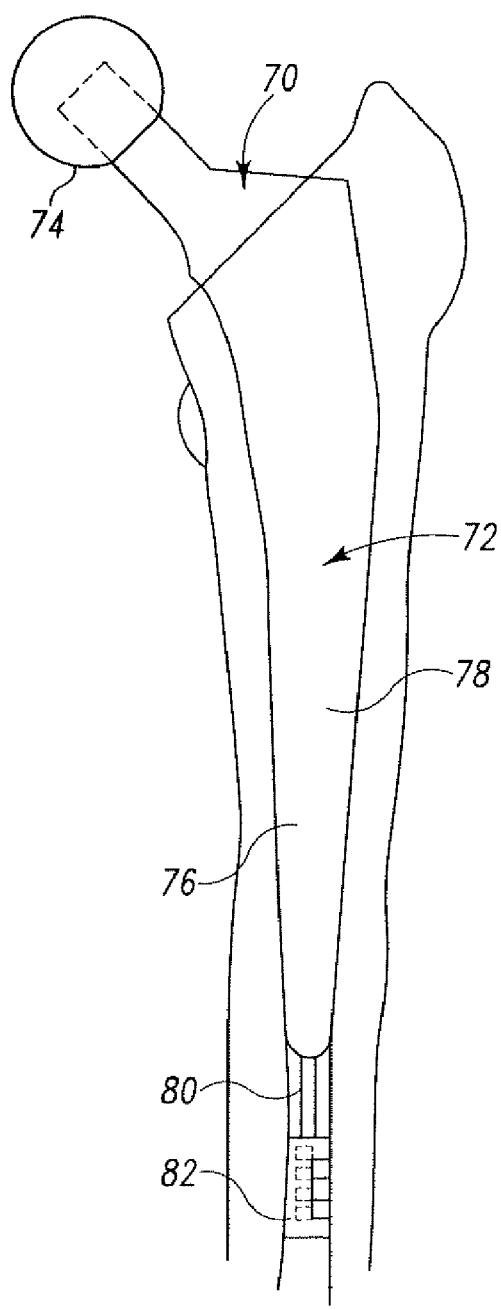
FIG. 7 is a diagrammatic illustration of a prosthetic proximal femoral implant implanted on the proximal femur in a non-cemented application, with the proximal femur shown in cross-section along a coronal plane, and with another embodiment of a fixed position reference member and a movable position reference member in position in the intramedullary canal.

An alternate embodiment of a proximal femoral system is illustrated in FIG. 7 at 70. The proximal femoral system 70 of FIG. 7 includes a proximal femoral implant component 72. As in the first illustrated proximal femoral implant component 15, the proximal femoral implant component 72 of the FIG. 7 system 70 includes a femoral head 74 and a femoral stem 76. The femoral head 74 comprises the articulating portion of the proximal femoral implant component 72 and the femoral stem 76 includes the fixation portion 78. The femoral head 74 is substantially spherical and is assembled with the femoral stem 76 in a standard manner. The proximal femoral implant system 70 also includes a movable femoral position reference member 80 and a fixed femoral position reference member 82.

The proximal femoral implant component 72 of the FIG. 7 system is for non-cemented use; accordingly, at least part of the outer surface of the fixation portion 78 of the femoral stem 76 may be porous. As used herein, "porous" refers to a surface that is conducive to bone ingrowth for non-cemented fixation, and "smooth" refers to a surface that is not conducive to such bone ingrowth. Suitable porous surfaces can be made by many different methods: casting, embossing, etching, milling, machining, and coating such as by plasma-spraying or by bonding, for example. Bonded materials can comprise sintered metal beads, sintered metal mesh or screen, or sintered metal fibers, for example. Known, commercially available materials and techniques can be used to create the porous exterior surfaces: for example, POROCOAT® coating, available from DePuy Orthopaedics, Inc. of Warsaw, Ind., could be used, as well as other commercially available coatings. It should be understood that the above-identified examples of materials, methods and commercial products are provided as examples only; the present invention is not limited to any particular material, method or commercial product for the porous surfaces unless expressly called for in the claims. In addition, it should be understood that as additional materials and methods become available to create surfaces that promote bony ingrowth, it is believed that such other materials and methods may also be useful with the present invention.

Figure 8:
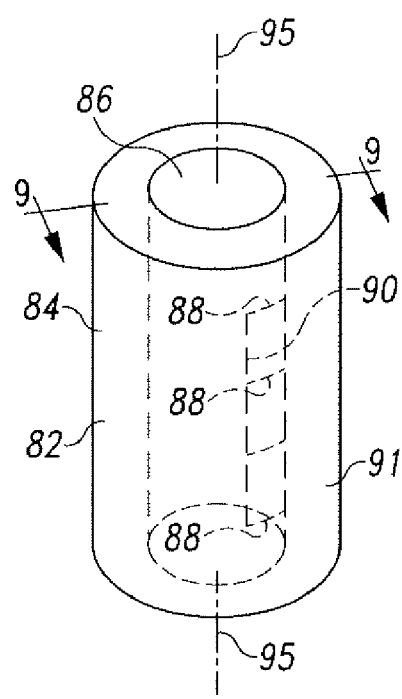
FIG. 8 is a perspective view of one possible fixed position reference member suitable for use in conjunction with an orthopaedic implant such as shown in FIG. 7.
Figure 9:
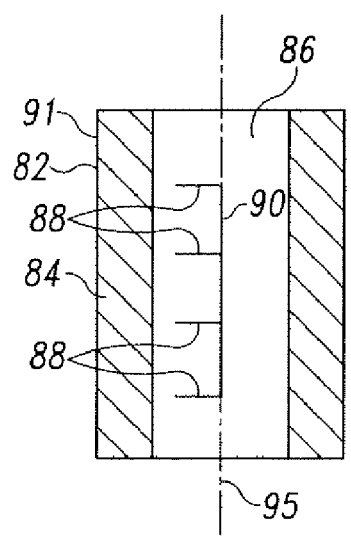
FIG. 9 is a cross-section of the fixed position reference member of FIG. 8, taken along line 9-9 of FIG. 8.

An example of a suitable fixed position reference member 82 for use in the embodiment of FIG. 7 is illustrated in FIGS. 8-9. This fixed position reference member 82 comprises a substantially cylindrical body 84 with an internal wall defining a cylindrical bore 86. The internal wall that defines the cylindrical bore 86 includes a plurality of transverse radio-opaque indicia 88 and a single radio-opaque longitudinal indicia 90. As in the first illustrated embodiment, the radio-opaque indicia 88, 90 could be formed of thin metal wire or other suitable radio-opaque material, such as a radio-opaque ink adhered to the inner wall. And as in the first illustrated embodiment, the transverse radio-opaque indicia 88 extend around only a portion of the inner wall that defines the bore 86 to avoid possible distortion from parallax.

The outer surface 91 of the fixed position reference member 82 may be porous so that the position of the fixed position reference member 82 in the intramedullary canal can ultimately be fixed through bony ingrowth. Alternatively or additionally, the fixed position reference member 82 may have movable fingers or other structures to engage the wall of the intramedullary canal upon or after implantation.

Examples of suitable movable position reference members are illustrated in FIGS. 10-12 as 80A, 80B and 80C. Each of these movable position reference members 80A, 80B, 80C comprises a distal, post portion 92 and a proximal connecting portion 94. The cylindrical portion 92 of each of these movable position reference members 80A, 80B, 80C is sized and shaped to be telescopically received in and longitudinally slidable within the bore 86 of the fixed position reference member 80. The post portion 92 of each of these movable position reference members 80A, 80B, 80C can also rotate within the bore 86 about the longitudinal axis 95 of the bore 86.

The connecting portion 94 of the each of these movable position reference members 80A, 80B, 80C of FIGS. 10-12 is provided for directly connecting the movable reference member 80 to the distal end of the femoral stem 76. For this connection, the femoral stem 76 may include a distal bore (not shown), and the movable reference member 80 may include suitable structures for locking the reference member to the femoral stem 76. The locking structures could include for example, a pair of spring clips 96, 98 as shown in the movable position reference members 80A, 80B of FIGS. 10-11, that are received in and engage the distal bore of the femoral stem. Alternatively, the connecting portion 94 of the movable reference member and the distal bore of the femoral stem could be tapered so that the femoral stem and movable reference member 80 can be locked together through friction (e.g., a Morse taper); the movable reference member 80C of FIG. 12 illustrates an example of a suitable tapered end 97 of a connecting portion. It should be understood that the illustrated examples of locking structures are provided as examples only; other locking structures or chemicals (such as adhesive) could be used if desired.

Each of the moveable position reference members 80A, 80B, 80C of FIGS. 10-12 also includes one or more transverse indicia 100. The moveable position reference members 80A and 80B of FIGS. 10-11 also include one or more longitudinal indicia 102. In the embodiment of FIG. 10, the transverse indicia 100 comprise a set of evenly spaced parallel lines of radio-opaque material, such as wires, ink or powder that are embedded within, imprinted upon or adhered to a radiolucent body 104; the longitudinal indicia 102 comprise a set of evenly-spaced, longitudinally-staggered parallel lines of radio-opaque material, such as wires, ink or powder that are embedded within, imprinted upon or adhered to the radiolucent body 104. In the embodiment of FIG. 11, the body 106 of the post includes a through-hole or fenestration 108 defined by walls; a radio-opaque wire is strung across the through-hole 108 in a transverse direction to define the transverse indicia 100 and a set of radio-opaque wires are strung across the through-hole in a longitudinal direction to define the longitudinal indicia 100. Because the through-hole 108 is open across a transverse dimension of the body 106, the through-hole is radiolucent and the wires extending across the through-hole should be visible fluoroscopically and radiographically. Accordingly, in the embodiment of FIG. 11, the body 106 of the moveable position reference member 80B may be made of a radio-opaque material such as metal. In the embodiment of FIG. 12, the body 110 of the movable position reference member 80C is made of a radio-opaque material with a plurality of evenly-spaced cut-outs defining the transverse indicia 100. Using the moveable position reference member 80C of FIG. 12, radiolucent areas adjacent to the cut-outs should be visible.

Provision of both transverse and longitudinal indicia on the movable position reference member, such as the indicia illustrated at 100 and 102 in FIGS. 10-11, is advantageous if it is desired to monitor possible undesired movement of an implant in more than one direction. If the fixed position reference member has at least one longitudinal indicia, such as that shown at 90 in the embodiment of FIGS. 8-9, relative changes in the positions of the fixed longitudinal indicia 90 and movable longitudinal indicia 102 can be used to determine whether the implant component (such as femoral stem 76) has twisted with respect to the bone (such as twisting in the intramedullary canal of the proximal femur). If the fixed position reference member also has at least one transverse indicia, such as those shown at 88 in FIGS. 8-9, then the same position reference members can be used to track undesired movement of the implant in two directions, both linearly and rotatively. It should be understood that one of the sets of indicia can comprise a main scale and the other set of indicia can comprise a complementary vernier scale; however, the invention is not limited to use of a vernier-type scale unless expressly called for in the claims.

Although in the embodiments of FIGS. 7-12 it is possible to track the extent of movement of the implant, both linearly and rotatively, it should be understood that a system could allow for tracking of rotative motion alone. If one of the position reference members has indicia in only the longitudinal direction, as shown at 111 in fixed position reference 82B of FIG. 13, then it is possible to track undesired rotative movement alone.

FIGS. 14-15 illustrate other examples of possible designs for fixed position reference members 82C, 82D that may be used. The fixed position reference member 82C of FIG. 14 comprises a body 112 with a substantially cylindrical outer wall and substantially cylindrical inner wall defining a cylindrical through-bore 113 to receive the post 92 of one of the movable position reference members such as reference member 80A of FIG. 10. The body 112 has a pair of diametrically-opposed openings 114, 115 that provide radio-lucent areas. Transverse indicia 116 comprise at least one radio-opaque wire extending across one of the openings 114 and longitudinal indicia 118 comprise at least one radio-opaque wire extending transversely across the opening 114. The remainder of the body may be made of either a radiolucent or radio-opaque material. If made of a radio-opaque material such as metal, the outer surface of the body may be textured to be conducive to bony ingrowth. The fixed position reference member 82D of FIG. 15 comprises a body 122 with two spaced prongs 123, 124 joined at one end by an annulus 125. One of the prongs 123 has a serrated edge defining a plurality of transverse indicia 126. Both prongs 123, 124 have straight edges that define longitudinal indicia 127. The prongs 123, 124 and annulus 125 of the body 122 may be made of a radio-opaque material such as metal, and the outer surfaces may be textured to be conducive to bony ingrowth. The spaces between the prongs 123, 124 are radiolucent so that the indicia 126 and 127 and radio-opaque indicia on the moveable position reference member can be viewed fluoroscopically and radiographically.

Figure 16:
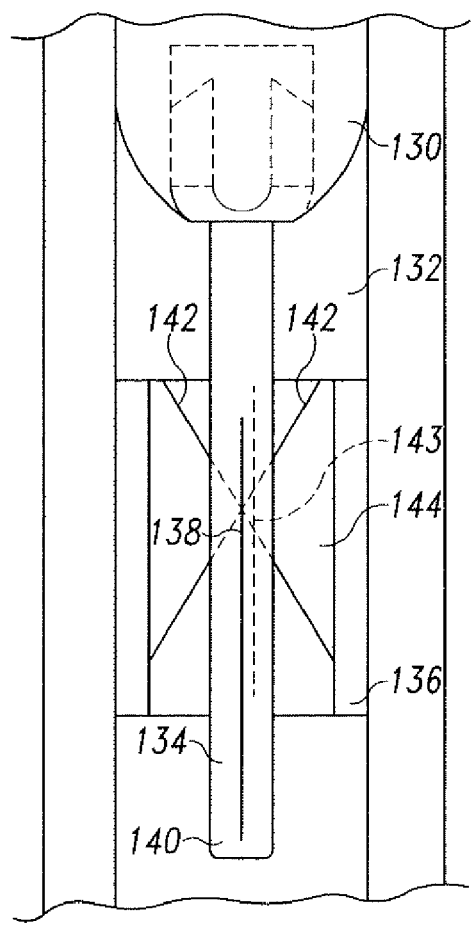
FIG. 16 is an elevation of another possible embodiment of a fixed position reference member and a movable position reference member shown in position at the end of a stem of an implant in the intramedullary canal of a bone, illustrating a possible orientation of the position reference members at one point in time.
Figure 17:
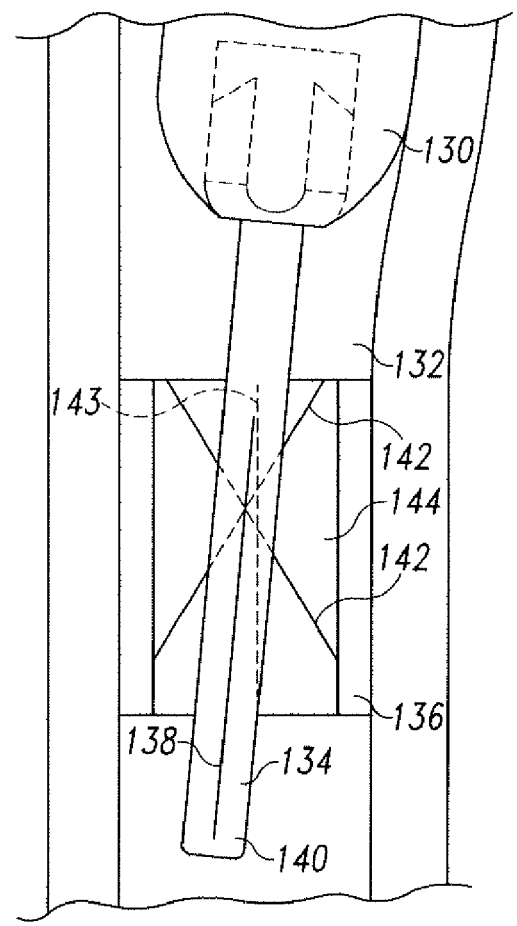
FIG. 17 is an elevation similar to that shown in FIG. 16, illustrating another possible orientation of the position reference members at a different point in time, illustrating how the present invention can be used to determine whether an implant has changed angular position over time.

The principles of the present invention should also prove usable in tracking any post-surgical pivotal movement of the implant. FIGS. 16-17 show a distal end of a stem implant component 130 received in an intramedullary canal 132. The movable position reference member 134 is affixed to the distal end of the stem 130 so that any movement of the stem 130 produces a corresponding movement of the movable position reference member 134. Part of the movable reference member 134 is received in a channel of a fixed position reference member 136. The moveable position reference member 134 has a single longitudinal radio-opaque indicia 138 and has a radiolucent body 140. The fixed position reference member 136 has a plurality of radio-opaque angled indicia 142, a single radio-opaque longitudinal indicia 143 and a radiolucent body 144. FIG. 16 illustrates an example of a possible starting position, for example, immediately post-surgery. FIG. 17 illustrates a stem implant that has pivoted about a transverse axis; the angular displacement of the stem implant can be evaluated and measured from the relationship between the longitudinal indicia 138 of the movable position reference member and the indicia 142, 143 of the fixed position reference member 136.

Figure 18:
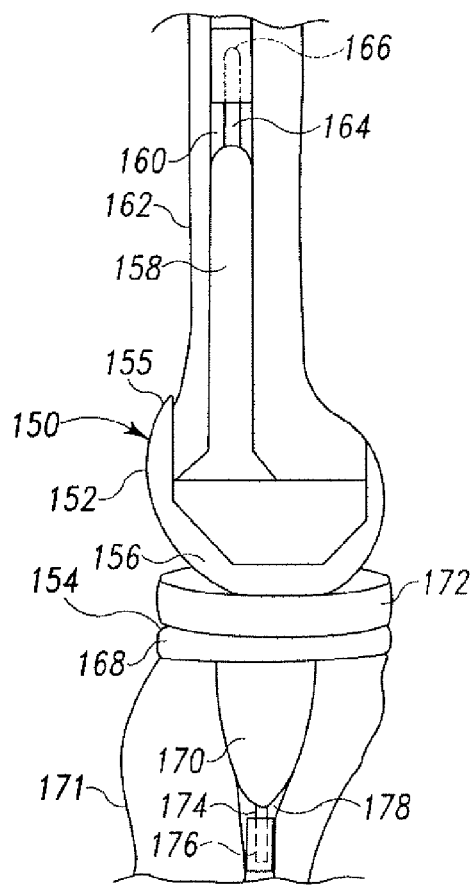
FIG. 18 is a diagrammatic illustration of a prosthetic knee joint implanted on the distal femur and proximal tibia, illustrating application of the principles of the present invention to knee implants.

It should be appreciated that the principles of the present invention can be applied to implants other than hip implants. FIG. 18 illustrates the principles of the present invention applied to a knee implant system and FIG. 19 illustrates the principles of the present invention applied to a shoulder implant system.

In FIG. 18, the illustrated knee joint endoprosthesis system 150 comprises a distal femoral system 152 and a proximal tibial system 154. The distal femoral system 152 comprises a femoral implant 155 with an articulating end 156 and a stem 158 received in the intramedullary canal 160 of the femur 162. The proximal end of the stem 158 is connected to a movable femoral position reference member 164 that is telescopically received in a fixed femoral position reference member 166. The proximal tibial implant system 154 comprises a tibial implant 168 having a stem 170 received in the tibia 171, a bearing 172 (typically ultrahigh molecular weight polyethylene), a movable tibial position reference member 174 and a fixed tibial position reference member 176 received in the intramedullary canal 178 of the tibia 171. All of the position reference members 164, 166, 174, 176 would have indicia to provide an indication of movement in at least one direction.

The femoral implant 155 and tibial implant 168 may have features of standard commercially available prosthetic knee joints, such as those available from DePuy Orthopaedics, Inc. of Warsaw, Ind. It should be understood that the present invention is expected to have application to the systems available from other suppliers of orthopaedic knee implants. In addition, the present invention is expected to have application to future knee implant systems as well as those presently available. Accordingly, the present invention is not limited to the system or configuration of any particular knee implant system unless expressly called for in the claims.

Figure 19:
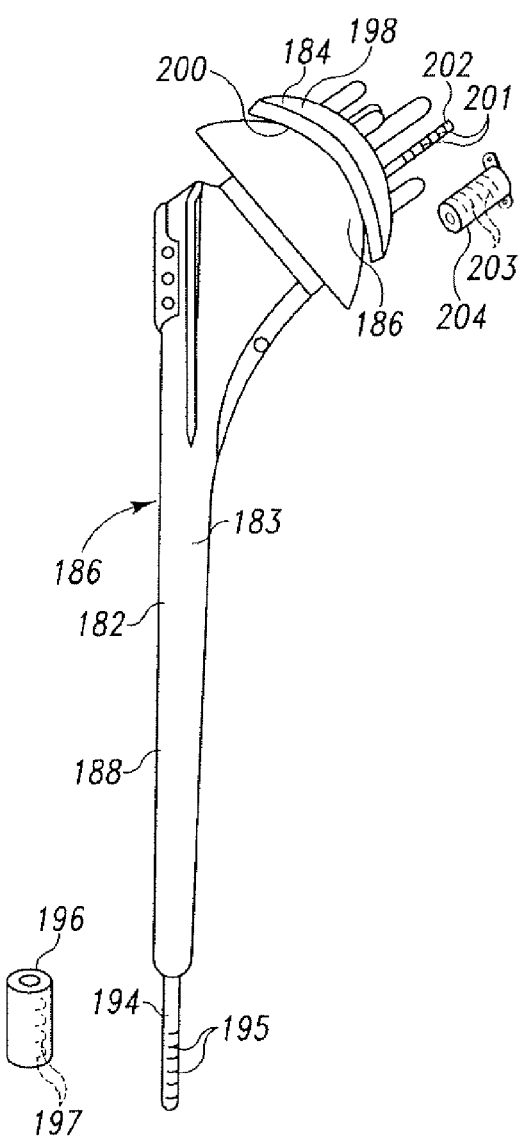
FIG. 19 is a diagrammatic illustration of a prosthetic shoulder joint illustrating application of the principles of the present invention to shoulder implants.

In FIG. 19, the illustrated shoulder joint endoprosthesis system 180 comprises a proximal humeral system 182 and a glenoid system 184. The proximal humeral system 182 comprises a humeral implant 183 having articulating end 186 and a stem 188 to be received in the intramedullary canal (not shown) of the humerus (not shown). The distal end of the stem 188 is connected to a movable humeral position reference member 194 that can be telescopically received in a fixed humeral position reference member 196. Both the movable humeral position reference member 194 and fixed humeral position member 196 have indicia 195, 197 that can be viewed fluoroscopically and radiographically. The glenoid implant system 184 comprises a glenoid component 198 having a bearing surface 200, a movable glenoid position reference member 202 and a fixed glenoid position reference member 204 to be received in part of the shoulder bone (not shown). Both the movable glenoid position reference member 202 and fixed glenoid position reference member 204 have indicia 201, 203 that can be viewed fluoroscopically and radiographically.

The movable position reference members 164, 174, 194, 202 may have features like those described above for the movable implant reference members 20, 32, 80, 80A, 80B, 80C, 134 of FIGS. 1-4, 7, 10-12 and 16-17. The fixed reference members 166, 176, 196, 204 may have features like those described above for the fixed position reference members 22, 82, 82B, 82C, 82D, 136 of FIGS. 1-4, 7-9 and 13-17, although it should be appreciated that the particular design chosen for the position reference members 164, 166, 174, 176, 194, 196, 202, 204 should be complementary to allow for fluoroscopic or radiographic viewing of the indicia of all the position reference members 164, 166, 174, 176, 194, 196, 202, 204.

The humeral implant 183 and glenoid implant 198 may have features of standard commercially available prosthetic shoulder joints, such as those available from DePuy Orthopaedics, Inc. of Warsaw, Ind. It should be understood that the present invention is expected to have application to the systems available from other suppliers of orthopaedic shoulder implants. In addition, the present invention is expected to have application to future shoulder implant systems as well as those presently available. Accordingly, the present invention is not limited to the system or configuration of any particular shoulder implant system unless expressly called for in the claims.

It should be appreciated that the principles of the present invention are expected to be applicable to other joint implant systems as well, such as ankle implant systems, elbow implant systems, and wrist implant systems, with features of such systems available from DePuy Orthopaedics, Inc. of Warsaw, Ind. as well as to such systems available from other suppliers of such implants. The principles of the present invention may also be applicable to other types of implants as well, such as spinal implants. In addition, the present invention is expected to have application to future implant systems as well as those presently available. Accordingly, the present invention is not limited to the system or configuration of any particular implant system unless expressly called for in the claims.

It should also be appreciated that for all of the illustrated movable and fixed position reference members, the components may be provided in a plurality of sizes to accommodate individual patient anatomy.

In use, the surgeon may prepare the bones for receipt of the implant components in a standard manner. The fixed position reference member 22, 23, 82, 82B, 82C, 82d, 136, 166, 176, 196, 204, or a temporary assembly of the fixed and movable position reference members as shown in FIG. 4, may be implanted in a prepared receptacle in the bone or in the intramedullary canal. If the movable position reference 20, 32, 80, 80A, 80B, 80C, 134, 164, 174, 194, 202 is to be connected to one of the implant components, the two parts can be assembled prior to implantation and then implanted. The surgeon may determine visually whether the movable position reference member 20, 32, 80, 80A, 80B, 80C, 134, 164, 174, 194, 202 is aligned to move with respect to the fixed position reference member 22, 23, 82, 82B, 82C, 82d, 136, 166, 176, 196, 204.

A baseline fluoroscopic or radiographic image may then be taken and maintained as a record. Periodically, such as annually, a new fluoroscopic or radiographic image may be taken and compared to the baseline image. By comparing the relative positions of the indicia of the fixed and movable position references 20, 22, 32, 34, 80, 80A, 80B, 80C, 82, 82B, 82C, 82D, 134, 136, 164, 166, 174, 176, 194, 196, 202, 204 in the two images, the surgeon can determine whether any undesirable movement has taken place between the implant and the bone. If the surgeon determines that significant undesirable movement has taken place, then surgical intervention may be required.

Various modifications and additions can be made to the above-described embodiments of the invention without departing from the spirit of the invention. For example, the lengths of the movable position reference members 80A, 80B, 80C of FIGS. 10-12 could be extended to allow more distance to exist between the implant component and the fixed position reference member; in addition, the movable position reference members 80A, 80B, 80C could be made of a flexible material to allow the surgeon greater choice in the positioning of the fixed position reference members. All such modifications and additions are intended to fall within the scope of the claims unless the claims expressly call for a specific construction.

I claim:

1. An implant system for fixation to a bone, the implant system comprising:

an implant component for fixation to the bone;

a first position reference member sized and shaped to be capable of being implanted proximate to the implant component;

a second position reference member sized and shaped to be capable of being implanted proximate to the first position reference member;

wherein the first position reference member and the second position reference member have longitudinal axes and are sized and shaped to be capable of relative movement;

wherein both the first position reference member and second position reference member include indicia and wherein the indicia and reference members are sized and shaped so that the first position reference member and second position reference member can be implanted in the bone with the indicia of the position reference members adjacent to each other;

wherein the first position reference member, second position reference member and indicia are sized, shaped and made of a material such that post-operative changes in the relative positions of the first position reference member and second position reference member can be determined by radiography or fluoroscopy;

wherein the indicia of one of the position reference members comprises a longitudinal main scale and the indicia of the other of the position reference members comprises a longitudinal vernier scale.

2. The implant system of claim 1 wherein the indicia comprising the main scale and indicia comprising the vernier scale are radio-opaque and a portion of the first position reference member and a portion of the second position reference member are radiolucent.

3. An implant system for fixation to a bone, the implant system comprising:

an implant component for fixation to the bone;

a first position reference member sized and shaped to be capable of being implanted proximate to the implant component, the first position reference member having a longitudinal axis and a radiolucent portion;

a second position reference member sized and shaped to be capable of being implanted proximate to the first position reference member, the second position reference member having a longitudinal axis and a radiolucent portion;

wherein the first position reference member and the second position reference member are sized and shaped to be capable of relative movement along their longitudinal axes;

wherein the first position reference member includes a radio-opaque scale comprising a plurality of transverse indicia aligned along the longitudinal axis of the first position reference member and the second position reference member includes includes a radio-opaque longitudinal vernier scale comprising a plurality of transverse indicia aligned along the longitudinal axis of the second position reference member;

wherein the main scale, vernier scale, first reference member and second reference members are sized and shaped so that the first position reference member and second position reference member can be implanted in the bone with the scale of one of the position reference members received within the other position reference member and with the main scale and vernier scale adjacent to each other;

wherein the first position reference member and second position reference member comprise discrete and separate components after implantation; and wherein the first position reference member, second position reference member, main scale and vernier scale are sized, shaped and made of a material such that post-operative changes in the relative positions of the first position reference member and second position reference member can be determined by radiography or fluoroscopy.

* * * * *